United States Patent
Eisler

(10) Patent No.: US 11,439,440 B2
(45) Date of Patent: Sep. 13, 2022

(54) VERTEBRAL DISC REPAIR

(71) Applicant: Innovasis, Inc., Salt Lake City, UT (US)

(72) Inventor: Jesse Eisler, Vernon, CT (US)

(73) Assignee: Innovasis, Inc., Salt Lake City, UT (US)

( * ) Notice: Subject to any disclaimer, the term of this patent is extended or adjusted under 35 U.S.C. 154(b) by 0 days.

(21) Appl. No.: 16/917,108

(22) Filed: Jun. 30, 2020

(65) Prior Publication Data

US 2020/0405357 A1 Dec. 31, 2020

Related U.S. Application Data

(60) Provisional application No. 62/868,958, filed on Jun. 30, 2019.

(51) Int. Cl.
*A61B 17/70* (2006.01)
*A61F 2/44* (2006.01)

(52) U.S. Cl.
CPC ...... *A61B 17/7053* (2013.01); *A61B 17/7001* (2013.01); *A61F 2/4455* (2013.01)

(58) Field of Classification Search
CPC ........... A61F 2/44–447; A61B 17/7053; A61B 17/7001
See application file for complete search history.

(56) References Cited

U.S. PATENT DOCUMENTS

| | | | | |
|---|---|---|---|---|
| 5,683,465 A * | 11/1997 | Shinn | A61F 2/30742 | 623/17.14 |
| 2002/0004683 A1 * | 1/2002 | Michelson | A61F 2/4455 | 623/17.16 |
| 2004/0243241 A1 * | 12/2004 | Istephanous | A61F 2/442 | 623/17.14 |
| 2006/0259147 A1 * | 11/2006 | Krishna | A61F 2/4425 | 623/17.15 |
| 2008/0215156 A1 * | 9/2008 | Duggal | A61F 2/42 | 623/18.11 |
| 2010/0217395 A1 * | 8/2010 | Bertagnoli | A61B 17/1604 | 623/17.16 |
| 2011/0137421 A1 * | 6/2011 | Hansell | A61F 2/4455 | 623/17.16 |
| 2012/0101579 A1 * | 4/2012 | de Villiers | A61F 2/4611 | 623/17.16 |
| 2012/0143336 A1 * | 6/2012 | Aflatoon | A61F 2/4465 | 623/17.16 |
| 2014/0296985 A1 * | 10/2014 | Balasubramanian | A61F 2/4684 | 623/17.16 |
| 2015/0039089 A1 * | 2/2015 | Balasubramanian | A61F 2/30767 | 623/17.15 |

(Continued)

FOREIGN PATENT DOCUMENTS

WO WO-2004002291 A2 * 1/2004 ........... A61F 2/4425

*Primary Examiner* — Nicholas J Plionis
(74) *Attorney, Agent, or Firm* — Brooks, Cameron & Huebsch, PLLC

(57) ABSTRACT

The present disclosure includes apparatuses, systems, and methods for vertebral disc repair. An example apparatus includes a first surface including a concave opening configured to receive an artificial disc, a second surface, and an aperture extending through the first surface and the second surface, wherein the aperture is configured to receive a bone screw.

16 Claims, 2 Drawing Sheets

(56) References Cited

U.S. PATENT DOCUMENTS

2018/0280156 A1* 10/2018 Dzioba ............... A61F 2/30771
2019/0008651 A1* 1/2019 Doty .................... A61F 2/4425

* cited by examiner

VERTEBRAL DISC REPAIR

PRIORITY INFORMATION

This application claims priority of U.S. Provisional Application Ser. No. 62/868,958, filed on Jun. 30, 2019, the content of which are incorporated herein by reference.

TECHNICAL FIELD

The present disclosure relates generally to vertebral disc repair, and more particularly, to replacing a disc with an artificial disc.

BACKGROUND

The human spine is a generally flexible column that can take tensile and compressive loads, allows bending motion and provides a place of attachment for ribs, muscles and ligaments. Generally, the spine is divided into three sections: the cervical, the thoracic, and the lumbar spine. The sections of the spine are made up of individual bones called vertebrae and the vertebrae are separated by intervertebral discs which are situated therebetween.

The vertebral discs function as shock absorbers and as joints. They are designed to absorb the compressive and tensile loads to which the spinal column may be subjected to while at the same time allowing adjacent vertebral bodies to move relative to each other a limited amount, particularly during bending (e.g., flexure) of the spine. Thus, the intervertebral discs are under constant muscular and/or gravitational pressure and generally are the first parts of the lumbar spine to show signs of "wear and tear".

The intervertebral disc is composed of an inner gel-like matrix called the nucleus pulposus and an outer surrounding fibrous band called the annulus fibrosus. When compressive loads are placed on the spine, increased pressure in the nucleus pulposus is transmitted to the annulus, which bulges outwards. The degenerative cascade of the vertebral disc initially involves desiccation of the nucleus pulposus. With decreased elasticity and dampening from the nucleus, increased loads are transmitted to the annulus. The increased stress on the annulus can lead to fissures and radial tears in its collagen fibers. With further degeneration, this can lead to circumferential bulging of the disc, contained and uncontained disc herniations, and complete desiccation of the disc. This degenerative cascade can result in axial pain, by stimulating pain fibers in the annulus, or compression of spinal nerve roots and/or the spinal cord. This can manifest itself in motor weakness, pain, and/or numbness in the arms and/or legs.

The structure and function of the discs may be altered by a variety of factors including repeated stress, trauma, infection, neoplasm, deformity, segmental instability, and inflammatory conditions. Degeneration of the intervertebral disc is the most common etiology of clinical symptoms referable to the spine. Degeneration of the spine is a universal concomitant of human aging. In the cervical spine, neck, and arm pain caused by nerve root compression has been estimated to affect 51% of the adult population. Spondylosis of the spine and aging are intimately related, with spondylosis increasing in both prevalence and severity with age. Fortunately, the majority of patients will improve without surgery. In approximately 10-15% of cases, spondylosis is associated with persistent nerve root and spinal cord compression and/or spinal pain, with a small percentage ultimately requiring surgery.

One surgical procedure for treating these conditions is spinal fusion, which can be performed anteriorly, posteriorly or laterally. These procedures result in the fusion of adjacent vertebrae. Solidly fusing a spinal segment to eliminate any motion at that level may alleviate the immediate symptoms, but for some patients maintaining motion may be advantageous.

DETAILED DESCRIPTION

Figure 1A:
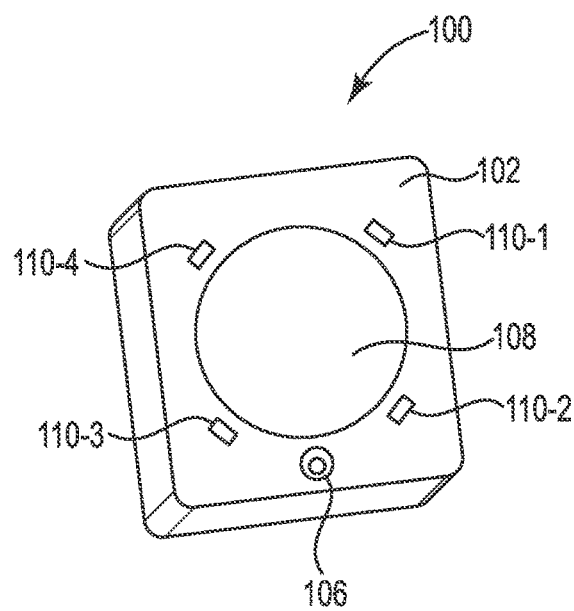
FIG. 1A is a schematic diagram of a first surface of a plate in accordance with a number of embodiments of the present disclosure.

The present disclosure includes apparatuses, systems, and methods for vertebral disc repair. An example apparatus includes a first surface including a concave opening configured to receive an artificial disc, a second surface, and an aperture extending through the first surface and the second surface, wherein the aperture is configured to receive a bone screw.

The artificial disc can provide a normal range of motion of the natural vertebral disc, along with the ability to correct deformities of the spine. The vertebral disc repair system allows for independent and mobile centers of rotation in the flexion-extension and lateral-bending motions. The system has durability and biocompatibility, and a means for integrating itself into the spine structure for long-term stability. In contrast to the existing disc replacement systems, it will allow the surgeon to correct deformities of the spine while maintaining the natural forces of the spine.

In a number of embodiments, the artificial disc is placed between two plates. One plate can be coupled to the superior or upper vertebra and the other plate can be attached to the inferior or lower vertebra. A bone screw can be used to attach a plate to a vertebra.

Each plate can include a first surface with a number of tabs and a second surface with a number of keels. The number of tabs can maintain the artificial disc in place while the number of keels can maintain the plate (e.g., vertebral disc repair apparatus) and/or vertebral disc repair system in place.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

It is to be understood that the terminology used herein is for the purpose of describing particular embodiments only and is not intended to be limiting. As used herein, the singular forms "a", "an", and "the" can include both singular and plural referents, unless the context clearly dictates otherwise. In addition, "a number of", "at least one", and "one or more" (e.g., a number of tabs) can refer to one or more tabs, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of an element of the system, as appropriate to the context.

The figures herein follow a numbering convention in which the first digit or digits correspond to the figure number and the remaining digits identify an element or component in the figure. Similar elements or components between different figures may be identified by the use of similar digits. For example, 112 may reference element "12" in FIG. 1B, and a similar element may be referenced as 312 in FIG. 3A. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1A is a schematic diagram of a first surface 102 of a plate 100 in accordance with a number of embodiments of the present disclosure. The first surface 102 of the plate 100 faces the artificial disc. Plate 100 can include an aperture 106, a concave opening 108, and a number of tabs 110-1, 110-2, 110-3, and 110-4.

In a number of embodiments, plate 100 can be made in a range of varying sizes and/or thicknesses to accommodate differences in anatomy. Plate 100 can be fabricated of titanium, titanium carbide, or a titanium alloy, cobalt-chrome-molybdenum (CoCrMo), cobalt chrome, stainless steel, metal matrix composites, or other materials suitable for spinal prosthetic inserts, for example. In some examples, coatings can be used on and/or included on plate 100 for accommodating bone ingrowth, lubricity, low-friction, enhanced hardness, low surface energy, roughness, or other desirable characteristics for an articulating joint. For example, the plate 100 can include a coating of porous titanium or calcium phosphate to promote bone ingrowth for long-term stability.

Figure 3A:
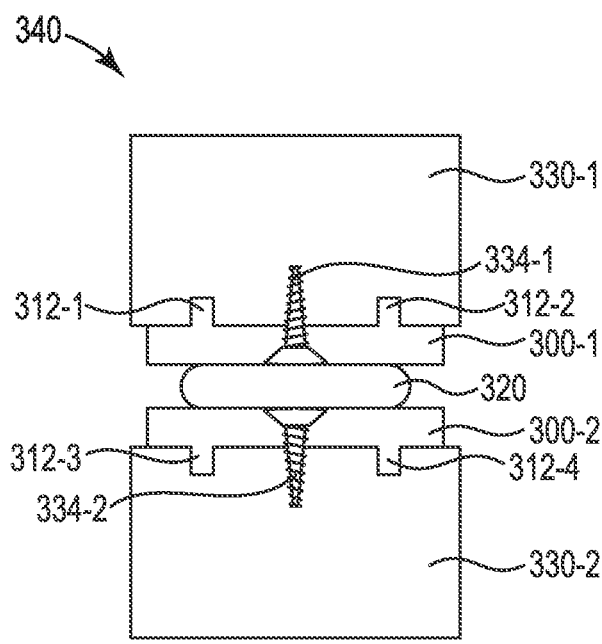
FIG. 3A is an anterior view of a vertebral disc repair system in accordance with a number of embodiments of the present disclosure.
Figure 3B:
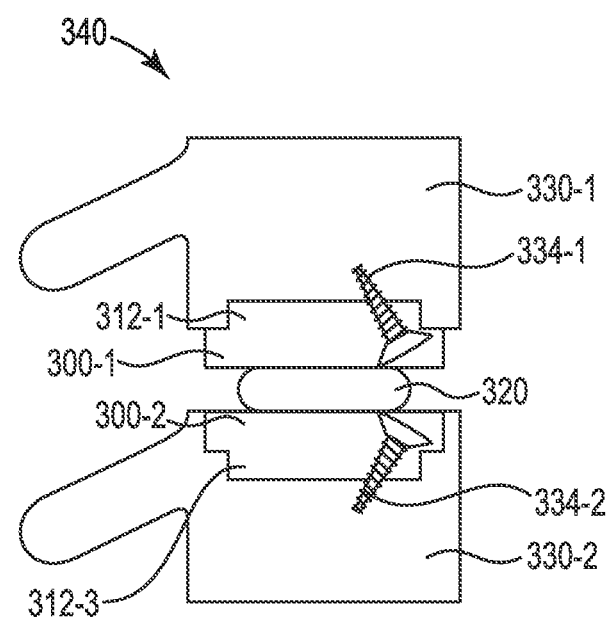
FIG. 3B is a lateral view of a vertebral disc repair system in accordance with a number of embodiments of the present disclosure.

Aperture 106 can extend through the first surface 102 and the second surface (e.g., second surface 104 in FIG. 1B) and can receive a bone screw (e.g., bone screw 334 in FIGS. 3A and 3B) to anchor the plate 100 to a vertebra (e.g., vertebra 330 in FIGS. 3A and 3B). For example, coupling the plate 100 to a vertebra can include inserting the bone screw through the aperture 106 of the plate 100 and screwing the bone screw into the vertebra. The diameter of the aperture 106 can be less than a diameter of a head of the bone screw. In some embodiments, aperture 106 can include a countersink to receive the head (e.g., top) of the bone screw so that the head of the bone screw is completely or mostly below the first surface 102 of plate 100. Aperture 106 can also include a locking mechanism such as a locking screw to prevent the bone screw from backing out after implantation. While only one aperture 106 is shown, in some embodiments plate 100 can have two, three, or four apertures 106, for example.

The first surface 102 of plate 100 can include concave opening 108 to receive an artificial disc (e.g., artificial disc 220 in FIGS. 2A and 2B) that fits into concave opening 108. The concave opening 108 can assist in holding the artificial disc in place. While concave opening 108 is shown as being symmetrical, it can be asymmetrical.

The tabs 110-1, 110-2, 110-3, and 110-4 can be projections that extend out from the first surface 102. The tabs 110-1, 110-2, 110-3, and 110-4 can maintain the artificial disc in place after the artificial disc is implanted in the vertebra. For example, the height of the tabs 110-1, 110-2, 110-3, and 110-4 can be such that they prevent the artificial disc from being squeezed out from between two plates after implantation, but the tabs 110-1, 110-2, 110-3, and 110-4 are not so tall that they interfere with an adjacent plate or with tabs on an adjacent plate. Although four tabs 110-1, 110-2, 110-3, and 110-4 are illustrated in FIG. 1A, the plate 100 may not include tabs 110-1, 110-2, 110-3, and 110-4 or can include any number of tabs 110-1, 110-2, 110-3, and 110-4. In some examples, the tab 110 can be in the shape of a ring and extend more than three-fourths of the way around concave opening 108.

Figure 1B:
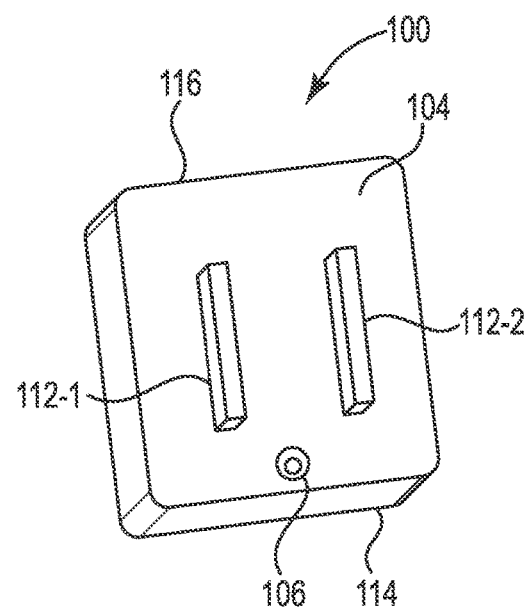
FIG. 1B is a schematic diagram of a second surface of a plate in accordance with a number of embodiments of the present disclosure.

FIG. 1B is a schematic diagram of a second surface 104 of a plate 100 in accordance with a number of embodiments of the present disclosure. The second surface 104 of the plate 100 faces a vertebra. Plate 100 can include an aperture 106 and a number of keels 112-1 and 112-2.

The number of keels 112-1 and 112-2 can be projection structures that extend out from the second surface 104 towards vertebra. The keels 112-1 and 112-2 can extend a majority of the way on a line between a posterior edge 116 and an anterior edge 114 or can be shorter in length such that the keels 112-1 and 112-2 only extend a small portion of the distance between the posterior edge 116 and the anterior edge 114. Although the keels 112-1 and 112-2 are illustrated as being perpendicular to plate 100, keels 112-1 and 112-2 can extend in a lateral or angled direction. The number of keels 112-1 and 112-2 can maintain the plate 100 (e.g., vertebral disc repair apparatus) and/or a vertebral disc repair system (e.g., vertebral disc repair system 340 in FIGS. 3A and 3B) in place and/or assist in attaching the plate 100 to vertebra. In some examples, the keels 112-1 and 112-2 can have a triangle profile and/or come to a point to sink into the vertebra to maintain the plate 100 and/or the vertebral disc repair system in place. Although two keels 112-1 and 112-2 are illustrated in FIG. 1B, the plate 100 may not include keels 112-1 and 112-2 or can include any number of keels 112-1 and 112-2.

Figure 2A:
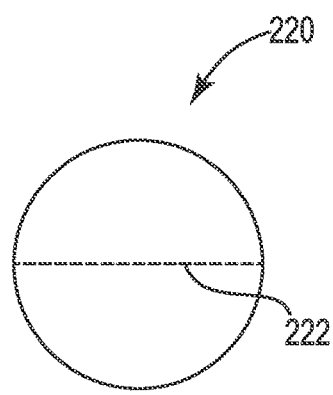
FIG. 2A is a top view of an artificial disc in accordance with a number of embodiments of the present disclosure.

FIG. 2A is a top view of an artificial disc 220 in accordance with a number of embodiments of the present disclosure. The artificial disc 220 can provide a normal range of motion of the natural vertebral disc, along with the ability to correct deformities of the spine.

The artificial disc 220 can be manufactured by, for example, casting, molding, thermoforming, extrusion molding, or 3D printing. The artificial disc 220 can be interchanged and revised intra-operatively and post-operatively. Instruments can be used to gauge the need for and amount of correction to determine the shape and size of the artificial disc 220 for a particular patient. For example, a surgeon can choose an artificial disc 220 that is an appropriate correction for a patient.

The artificial disc 220 can be constructed from a biocompatible material, a metal, metal matrix composites, metal alloys, metal coated with a polymer, a polymer, a ceramic or a low friction elastomer. For example, the artificial disc 220 can be composed of polyurethane, polycarbonate-polyurethane, polyethylene, high density polyethylene (HDPE), ultra-high molecular weight polyethylene (UHMWPE), titanium carbide, titanium, titanium alloy, chrome-cobalt-molybdenum (CoCrMo), cobalt chrome, stainless steel, or other suitable materials.

Although the artificial disc 220 is illustrated as a circular shape in FIG. 2A, the artificial disc 220 can be symmetrical or asymmetrical and can be in the shape of an ovoid, spheroid, ellipsoid, or a partially squashed sphere, for example. In a number of embodiments, the artificial disk 220 can treat disc/vertebral body disease, lordosis, kyphosis, and/or scoliosis using a particular shaped artificial disc 220.

The artificial disc 220 can include a horizontal axis 222. The horizontal axis 222 of the artificial disk 220 may not be located at a geometric center of the disc 220. For example, the horizontal axis may be located based on the type of deformity that needs to be corrected.

Figure 2B:
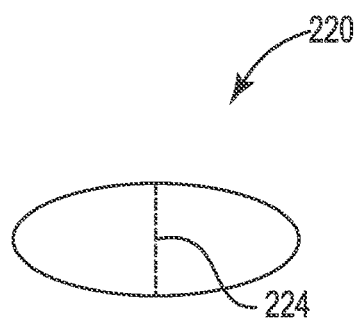
FIG. 2B is a side view of an artificial disc in accordance with a number of embodiments of the present disclosure.

FIG. 2B is a side view of an artificial disc 220 in accordance with a number of embodiments of the present disclosure. The artificial disc 220 can provide a normal range of motion of the natural vertebral disc, along with the ability to correct deformities of the spine.

The artificial disc 220 can include a vertical axis 224. The maximum vertical axis 224 of the artificial disc 220 may not be located at the geometric center of the artificial disc 220. The maximum vertical axis may be located toward the front of the artificial disc 220, the rear of the artificial disc 220, and/or on one side of the artificial disc 220. The positioning of the maximum vertical height and load bearing capability is chosen depending on the type of deformity that needs to be corrected.

FIG. 3A is an anterior view of a vertebral disc repair system 340 in accordance with a number of embodiments of the present disclosure. In some examples, the vertebral disc repair system 340 can be totally contained within the cylinder of the spine of a patient with no pieces of the vertebral disc repair system 340 extending outside the vertebra 330. The vertebral disc repair system 340 includes plate 300-1, plate 300-2, artificial disc 320, bone screw 334-1, and bone screw 334-2.

Plate 300-1 and/or plate 300-2 can be made in a range of varying sizes and/or thicknesses to accommodate differences in anatomy. Plate 300-1 and/or plate 300-2 can be fabricated of titanium, titanium carbide, or a titanium alloy, cobalt-chrome-molybdenum (CoCrMo), cobalt chrome, stainless steel, metal matrix composites, or other materials suitable for spinal prosthetic inserts, for example. In some examples, coatings can be used on and/or included on plate 300-1 and/or plate 300-2 for accommodating bone ingrowth, lubricity, low-friction, enhanced hardness, low surface energy, roughness, or other desirable characteristics for an articulating joint. For example, plate 300-1 and/or 300-2 can include a coating of porous titanium or calcium phosphate to promote bone ingrowth for long-term stability.

In a number of embodiments, plate 300-1 can include keel 312-1 and 312-2 and plate 300-2 can include keel 312-3 and 312-4. The number of keels 312-1, 312-2, 312-3, and 312-4 can be projection structures that extend out from the second surface (e.g., second surface 104 in FIG. 1B) towards vertebra 330. The keels 312-1, 312-2, 312-2, and 312-4 can extend a majority of the way on a line between a posterior edge (e.g., posterior edge 116 in FIG. 1B) and an anterior edge (e.g., anterior edge 114 in FIG. 1B) or can be shorter in length such that the keels 312-1, 312-2, 312-2, and 312-4 only extend a small portion of the distance between the posterior edge and the anterior edge. In some examples, the keels 312-1, 312-2, 312-2, and 312-4 can extend in a lateral or angled direction. The number of keels can maintain plate 300-1, plate 300-2, and/or the vertebral disc repair system 340 in place and/or assist in attaching plate 300-1 to vertebra 330-1 and plate 300-2 to vertebra 330-2. Although plate 300-1 includes two keels 312-1 and 312-2 and plate 300-2 includes two keels 312-3 and 312-4, plate 300-1 and/or 300-2 may not include a keel 312 or can include any number of keels 312.

The artificial disc 320 can provide a normal range of motion of the natural vertebral disc, along with the ability to correct deformities of the spine. The artificial disc 320 can be manufactured by, for example, casting, molding, thermoforming, extrusion molding, or 3D printing. The disc 320 can be interchanged and/or revised intra-operatively and post-operatively. Instruments can be used to gauge the need for and amount of correction to determine the shape and size of the disc 320 for a particular patient. For example, a surgeon can choose an artificial disc 320 that is an appropriate correction for a patient.

The artificial disc 320 can be constructed from a biocompatible material, a metal, metal matrix composites, metal alloys, metal coated with a polymer, a polymer, a ceramic, or a low friction elastomer. For example, the artificial disc 320 can be composed of polyurethane, polycarbonate-polyurethane, polyethylene, high density polyethylene (HDPE), ultra-high molecular weight polyethylene (UHMWPE), titanium carbide, titanium, titanium alloy, chrome-cobalt-molybdenum (CoCrMo), cobalt chrome, stainless steel, or other suitable materials.

Bone screws 334-1 and 334-2 can be fasteners with an external thread. A bone screw 334 can be used to attach a plate 300 to a vertebra 330. For example, bone screw 334-1 can be inserted into an aperture (e.g., aperture 106 in FIGS. 1A and 1B) of plate 300-1 and screwed into vertebra 330-1 and bone screw 334-2 can be inserted in an aperture of plate 300-2 and screwed into vertebra 330-2.

Spinal deformity can be treated using the vertebral disc repair system 340. A spinal segment can be prepared for implantation of the artificial disc 320, a desired angle of the intervertebral space can be determined, an artificial disc 320 (e.g., an artificial nucleus) having the desired dimensions can be selected, a disc can be removed, plate 300-1 can be coupled (e.g., affixed) to vertebra 330-1 (e.g., upper vertebra or superior vertebra), plate 300-2 can be coupled to the vertebra 330-2 (e.g., lower vertebra or inferior vertebra), and the selected artificial disc 320 can be inserted between plate 300-1 and plate 300-2. The artificial disc 320 inserted between plate 300-1 and plate 300-2 can include inserting the artificial disc 320 between a concave opening (e.g., concave opening 108 in FIG. 1A) of plate 300-1 and a concave opening of plate 300-2. In some examples coupling plate 300-1 to vertebra 330-1 includes inserting bone screw 334-1 through an aperture of plate 300-1 and screwing the bone screw 334-1 into vertebra 330-1 and coupling plate 300-2 to vertebra 330-2 includes inserting bone screw 334-2 through an aperture of plate 300-2 and screwing the bone screw 334-2 into vertebra 330-2.

Alternatively, the assembled vertebral disc repair system 340 including the plate 300-1, artificial disc 320, and plate 300-2 can be inserted in unison. The configuration of the artificial disc 320 in this pre-assembled construct can be determined by intra-operative measurement tools, or with pre-operative calculations. Pre-operative planning techniques and instruments may also be able to determine the size and orientation of this device for insertion.

The vertebral disc repair system 340 allows the artificial disc 320 to be easily and rapidly inserted and the artificial disc 320 to be changed or revised in accordance with the magnitude of the deformity being corrected. This is especially useful in children and young adults where the alignment of the spine changes over time.

In some examples, the artificial disc 320 can be asymmetric for lordotic correction of the cervical spine. The surgeon can restore lordosis to the cervical spine while maintaining motion. The anterior height of the artificial disc 320 varies, depending on the extent of lordotic correction needed. The disc may be available in various lordotic angles (e.g., 0°, 3° and 6°), as well as differing heights (e.g., 4, 6, and 8 mm). In some examples, a concave opening of plate 300-1 and/or plate 300-2 can be shaped to fit an asymmetric artificial disc. For example, the concave opening may not be circular with the deepest point in the center of the concave opening.

While the vertebral disc repair system 340 illustrated in FIG. 3A includes a three-piece protheses with two plates 300-1 and 300-2 and an artificial disc 320, artificial disc 320 could be integrated with one of the plates 300-1 or 300-2 to provide a two-piece protheses. In some examples, a vertebral surface may be augmented by re-shaping the surface to accommodate the artificial disc 320.

FIG. 3B is a lateral view of a vertebral disc repair system in accordance with a number of embodiments of the present disclosure. In some examples, the vertebral disc repair system 340 can be totally contained within the cylinder of the spine of a patient with no pieces of the vertebral disc repair system 340 extending outside the vertebra 330. The vertebral disc repair system 340 includes plate 300-1, plate 300-2, artificial disc 320, bone screw 334-1, and bone screw 334-2.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A vertebral disc repair apparatus, comprising:
   a first plate, comprising:
      a first surface including a first concave opening configured to receive an artificial disc;
      a second surface, wherein the first concave opening is between the first surface and the second surface, wherein the first surface and the second surface are planar and parallel to each other and extend to each outer edge of the first plate, and wherein the first concave opening is configured to receive the artificial disc between the first surface and the second surface of the first plate and above the first surface of the first plate; and
      a first aperture extending through the first surface and the second surface, wherein the first aperture is configured to receive a first bone screw; and
   a second plate comprising:
      a third surface including a second concave opening configured to receive the artificial disc;
      a fourth surface, wherein the second concave opening is between the third surface and the fourth surface, wherein the third surface and the fourth surface extend to each outer edge of the second plate, wherein the second concave opening is configured to receive the artificial disc between the third surface and the fourth surface of the second plate and above the third surface of the second plate, and wherein the second plate includes at least one tab that extends out from the third surface towards the first plate; and
      a second aperture extending through the third surface and the fourth surface, wherein the second aperture is configured to receive a second bone screw.

2. The apparatus of claim 1, wherein the third first surface includes the at least one tab and a number of other tabs.

3. The apparatus of claim 1, wherein the at least one tab maintains the artificial disc in place.

4. The apparatus of claim 1, wherein the second surface includes at least one keel.

5. The apparatus of claim 4, wherein the at least one keel maintains the vertebral disc repair apparatus in place.

6. The apparatus of claim 1, wherein a diameter of the first aperture is less than a diameter of a head of the first bone screw.

7. The apparatus of claim 6, wherein the first aperture includes a countersink to receive the head of the first bone screw.

8. A vertebral disc repair system, comprising:
   an artificial disc, wherein the artificial disc is symmetrical;
   a plate including:
      a concave opening configured to receive the artificial disc, wherein the concave opening is between a first surface and a second surface of the plate, wherein the first surface and the second surface are planar and parallel to each other and extend to each outer edge of the first plate, and wherein the artificial disc is located between the first surface and the second surface of the plate and above the first surface of the plate, wherein the plate includes at least one tab that extends out from the first surface;
      an aperture extending through the plate, wherein the aperture is configured to receive a bone screw; and
      the bone screw configured to couple the plate to a vertebra; and
   a different plate including:
      a different concave opening configured to receive the artificial disc, wherein the different concave opening is between a third surface and a fourth surface of the different plate, wherein the third surface and the fourth surface are planar and parallel to each other and extend to each outer edge of the different plate, and wherein the artificial disc is located between the third surface and the fourth surface of the different plate and above the third surface of the different plate, wherein the different plate includes at least one tab that extends out from the third surface towards the first surface of the plate;

a different aperture extending through the different plate, wherein the different aperture is configured to receive a different bone screw; and the different bone screw is configured to couple the different plate to a different vertebra.

9. The system of claim 8, wherein the artificial disc comprises high density polyethylene.

10. The system of claim 8, wherein the artificial disc is at least one of: an ovoid, spheroid, or ellipsoid.

11. The system of claim 8, wherein the artificial disc is 3D printed.

12. The system of claim 8, wherein the plate includes a coating that promotes bone growth.

13. The system of claim 8, wherein the artificial disc is specific to a patient.

14. The system of claim 8, wherein a position of a maximum vertical height of the artificial disc is based on a type of deformity.

15. A method for vertebral disc repair, comprising:
removing a disc;
coupling a first plate to a first vertebra;
coupling a second plate to a second vertebra; and
inserting an artificial disc between the first and second plates and into a first concave opening of the first plate and a second concave opening of the second plate, wherein the artificial disc is between a first surface and a second surface of the first plate and the artificial disc is between a third surface and a fourth surface of the second plate and wherein the first surface and the second surface are planar and parallel to each other and extend to each outer edge of the first plate and the third surface and the fourth surface are planar and parallel to each other and extend to each outer edge of the second plate and wherein the first plate includes at least one tab that extends out from the first surface toward the second plate.

16. The method of claim 15, wherein coupling the first plate to the first vertebra includes inserting a first bone screw through a first aperture of the first plate and screwing the first bone screw into the first vertebra and coupling the second plate to the second vertebra includes inserting a second bone screw through a second aperture of the second plate and screwing the second bone screw into the second vertebra.

* * * * *